United States Patent [19]

Ezzell et al.

[11] Patent Number: 4,578,512
[45] Date of Patent: Mar. 25, 1986

[54] PROCESS TO PRODUCE NOVEL FLUOROCARBON VINYL ETHERS AND RESULTING POLYMERS

[75] Inventors: Bobby R. Ezzell, Lake Jackson; William P. Carl, Angleton; William A. Mod, Lake Jackson, all of Tex.

[73] Assignee: The Dow Chemical Company, Midland, Mich.

[21] Appl. No.: 345,894

[22] Filed: Feb. 4, 1982

Related U.S. Application Data

[63] Continuation of Ser. No. 158,532, Jun. 11, 1980, abandoned.

[51] Int. Cl.$^4$ .................. C07C 69/65; C07C 69/52
[52] U.S. Cl. .................... 562/586; 260/544 F; 260/544 Y; 260/543 R; 260/543 F; 260/543 P; 260/513 F; 260/502.4 R; 260/501.15; 564/12; 564/96; 564/204; 558/449; 558/379; 558/410
[58] Field of Search ........... 260/543 F, 543 R, 513 F, 260/513 R, 501.15, 543 P, 465.6, 544 F, 544 Y, 502.4 R, 950; 564/12, 14, 96, 97, 201, 202, 203; 560/145, 183; 562/586

[56] References Cited

U.S. PATENT DOCUMENTS

| | | | |
|---|---|---|---|
| 4,085,071 | 4/1978 | Resnick et al. | 260/22 R |
| 4,138,426 | 2/1979 | England | 260/465.6 |
| 4,153,804 | 5/1979 | Yamabe et al. | 560/183 |
| 4,209,635 | 6/1980 | Munekata et al. | 560/183 |

FOREIGN PATENT DOCUMENTS 2029827 3/1980 United Kingdom .

*Primary Examiner*—Nicky Chan
*Attorney, Agent, or Firm*—James H. Dickerson

[57] ABSTRACT

Novel vinyl ethers are prepared in decarboxylation reactions of novel acid fluoride compounds according to the following reaction:

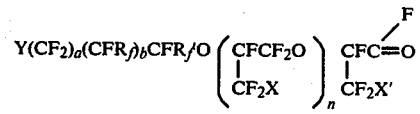

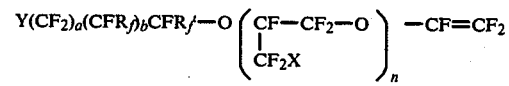

wherein
a is 0 or an integer greater than 0;
b is 0 or an integer greater than 0;
n=1 or an integer greater than 1;
$R_f$ and $R_f'$ are independently selected from the group consisting of F, Cl, perfluoroalkyl or fluorochloroalkyl;
X=F, Cl, Br or mixtures thereof when n>1
X'=Cl or Br;
Y is an acid group or an acid derivative easily convertible to an acid group;
Z=F, Cl, Br, OH, NRR' or OA;
R and R' are independently selected from the group consisting of hydrogen, an alkyl having one or more than one carbon atoms, and aryl; and
A=alkali metal, quaternary nitrogen, or R.

These vinyl ethers may be homopolymerized with themselves or copolymerized with other vinyl ethers.

9 Claims, No Drawings

PROCESS TO PRODUCE NOVEL FLUOROCARBON VINYL ETHERS AND RESULTING POLYMERS

CROSS REFERENCE TO RELATED APPLICATION

This is a continuation of our co-pending application Ser. No. 158,532, filed June 11, 1980, now abandoned.

BACKGROUND OF THE INVENTION

U.S. Pat. No. 3,282,875 shows the following decarboxylation reaction

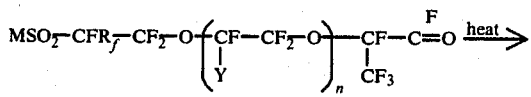

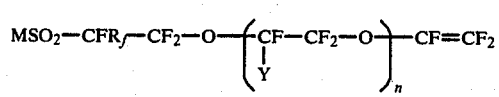

where
- $R_f$ is F or a perfluoroalkyl radical having from 1-10 carbon atoms;
- y is F or trifluoromethyl radical;
- n is an integer of 1-3, inclusive;
- M is F, hydroxyl radical, amono radical or OMe; and
- Me is an alkali metal or a quaternary nitrogen radical.

Yields in the decarboxylation reaction of about 80% were obtained at high temperatures (about 300° C.) while yields of 20-30% were obtained at lower temperatures (about 200° C.). Also taught is the homo and copolymerization of the vinylether monomers to form useful polymers.

British Pat. No. 1,518,387 teaches the following reactions

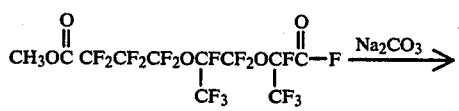

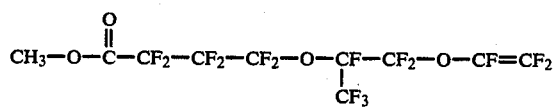

Copolymers of the vinylether monomers with tetrafluoroethylene were shown to be useful as membranes in chlor-alkali electrolytic cells.

Fearn, et al. *Journal of Polymer Science*, Volume 4, pp. 131-140, "Polymers and Terpolymers of Perfluoro-1,4-pentadiene" discloses that in the pyrolysis of sodium salts of carboxylic acids which contain fluorine and chlorine in the β position, sodium chloride is preferentially, but not exclusively eliminated. For example

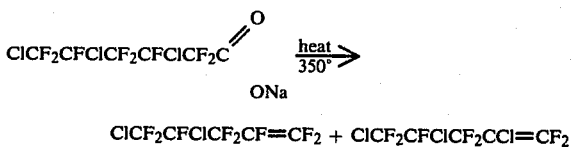

$$ClCF_2CFClCF_2CF=CF_2 + ClCF_2CFClCF_2CCl=CF_2$$

German Pat. No. 1,238,458 teaches that useful polymers are made from compounds of the general structure

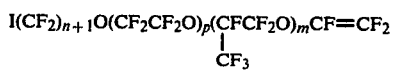

where n=1-8, p=0-5 and m=0-5. Crosslinked halogenated olefin copolymers are produced making use of the iodine group as a reactive site.

R. D. Chambers, in his book, *Fluorine in Organic Chemistry*, published by John Wiley & Sons, 1973, pages 211-212, teaches that carboxylic acid derivatives may be converted to olefins. The conversion is taught to involve the loss of carbon dioxide and formation of an intermediate carbanion. The intermediate then looses NaF to form the resulting olefin.

Numerous patents and publications have taught the use of acid functional fluorocarbon polymers in chlor-alkali electrolytic cells (British Pat. Nos. 1,497,748; 1,497,749; 1,518,387 and U.S. Pat. Nos. 3,784,399; 3,969,285; 4,025,405).

BRIEF DESCRIPTION

Novel compounds are prepared by decarboxylation of carboxylic acid derivatives according to the following reaction:

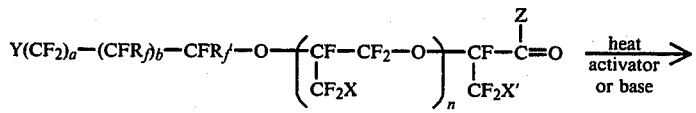

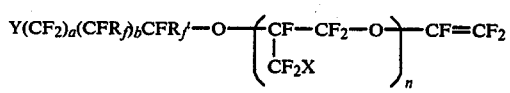

where
- a=0 or an integer greater than 0
- b=0 or an integer greater than 0
- n=1 or an integer greater than 1;
- $R_f$ and $R_f'$ are independently selected from the group consisting of F, Cl, perfluoroalkyl or fluorochloroalkyl;
- X=F, Cl, Br or mixtures thereof when n>1
- X'=Cl or Br;
- Y is an acid group or an acid derivative easily converted to an acid group;
- Z=F, Cl, Br, OH, NRR' or OA;
- R and R' are independently selected from the group consisting of hydrogen, an alkyl having one or more than one carbon atoms, and aryl; and
- A=alkali metal, quaternary nitrogen, or R.

These vinyl ethers may be homo polymerized with themselves or copolymerized with other vinyl ethers.

DETAILED DESCRIPTION

Novel compounds are prepared by decarboxylation of carboxylic acid derivatives according to the following reaction:

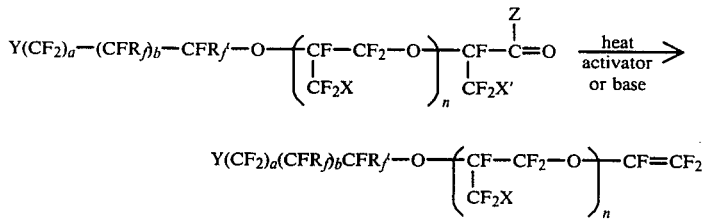

wherein
- a is 0 or an integer greater than 0;
- b is 0 or an integer greater than 0;
- n is one or an integer greater than one;
- $R_f$ and $R_{f'}$=are independently selected from the group consisting of F, Cl, perfluoroalkyl and fluorochloroalkyl;
- X=F, Cl, Br or mixtures thereof when n>1;
- X'=Cl or Br;
- Y is an acid group or an acid derivative easily convertible to an acid group.
- Z=F, Cl, Br, OH, NRR' or OA;
- R and R'=are independently selected from the group consisting of hydrogen, an alkyl having one or more than one carbon atoms, and aryl; and
- A=alkali metal, quaternary nitrogen, or R.

A variety of conditions usually involving a base are generally used for the decarboxylation reaction. Direct reaction of the above compound where Z=F with sodium carbonate as a slurry in a solvent such as glyme, diglyme or tetraglyme is particularly simple. Other methods are pyrolysis of the compound where Z=OH or ONa and reaction of the Z=F compounds with hot $K_2SO_4$ or $Na_2SO_4$ or pyrolysis with ZnO or Silica. Water alone converts the compound directly to the carboxylic acid which can be pyrolyzed. It is generally accepted that conversion of carboxylic acids or derivatives to olefins involves loss of carbon dioxide to form an intermediate carbanion. In the present case producing the following reactive intermediate

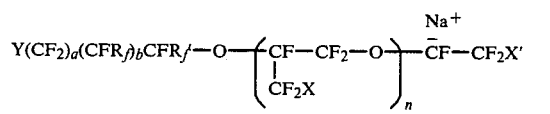

This reactive intermediate then loses NaX' to form the resulting olefin (monomer). At this point it is also possible to lose NaF which would result in formation of a X'(Cl, Br) substituted olefin, i.e.,

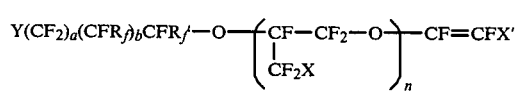

While it is not particularly surprising that loss of NaX' predominates, it is surprising that loss of NaX' as opposed to NaF is the sole detected course of the reaction, particularly when X'=Cl. Loss of NaF, while not being favored over loss of NaX', does readily occur from similar carbanion intermediates (U.S. Pat. No. 3,282,875). Indeed, Fearn discloses that in the decarboxylation of the structure shown below, elimination of NaCl predominates, but is not exclusive.

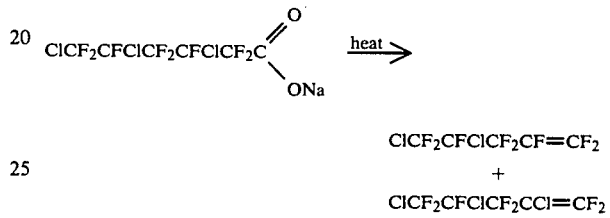

$ClCF_2CFClCF_2CF=CF_2$
+
$ClCF_2CFClCF_2CCl=CF_2$

Analysis of the vinyl ethers produced by the present invention by VPC, I.R., mass spectroscopy and F 19 NMR failed to detected the presence of any-~OCF=CFCl.

The above discussion describes a theory as to how the reactions proceed but in no way limits nor defines the scope of the invention.

Y is an acid group or an acid derivative easily convertible to an acid group. Y may be $SO_2$—Z,

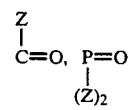

or C≡N or other appropriate groups groups. (As Z is defined above).

When polymers made from the vinyl ether monomers of the present invention are to be formed into sheets for use as membranes, such as in chlor-alkali cells, it is desirable to choose Z so that the polymers formed are thermoplastic to allow fabrication by conventional means, such as melt extrusion, but after fabrication can be easily converted to the acid or alkali metal salt of the acid. As an example, when Y=$SO_2F$ (Z=F), the intermediate is converted to an olefin monomer still having the —$SO_2F$ groups. The monomer is in turn copolymerized to form a polymer containing the $SO_2F$ group that can be formed into sheet by various plastic fabrication techniques.

After fabrication, the $SO_2F$ group is easily converted to the alkali metal salt of the corresponding sulfonic acid, —$SO_2ONa$ (Z=ONa), which can be converted to the sulfonic acid, —$SO_2OH$ (Z=OH), by reaction with acids, such as mineral acids.

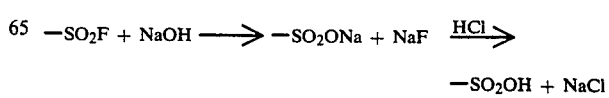

When Y is chosen as —C≡N, a nitrile, the above conditions are met since it is well known that nitriles are converted to carboxylic acids by hydrolysis.

When the polymers derived from the present monomer intermediates are to be used in particle or powder form, such as for acid catalyst, it is not critical in the choice of Z since fabrication is not as large a factor. In this case, Z can conveniently be any of the radicals listed. It can be —OH so as to directly have Y as an acid group or it can be any group rendering Y convertible to an acid group by further reaction.

The radical X is chosen from the halogens Cl, Br or F, while X' is chosen from Cl or Br. While iodine would also be a useful radical for X or X', formation of the ethers by the chemistry taught herein is hampered by side reactions causing low or nonexistant yields to the desired compounds.

When X'=Cl or Br and X=F, Cl or Br, new uses and novel and surprising new chemistry results from using the intermediates for additional chemical reactions. The prior art teaches that when Y=$SO_2F$, n=0 and X'=F (U.S. Pat. No. 3,560,568) reaction of the intermediate with base does not produce the desired vinyl ether monomer, but rather a cyclic sulfone compound. Surprisingly, when n=0, Y=$SO_2F$ and X'=Cl or Br, reaction of the intermediate with base produces the desired vinyl ether product in one step. In addition to this benefit, choosing X'=Cl or Br and X=Cl or Br in compounds when n>0 results in introducing a potential reaction site into polymers ultimately derived from monomers made from these intermediates. When n>0 both an acid site for ion exchange or catalyst and a reaction site for further reaction can be obtained by having X=Cl or Br and making a copolymer or homopolymers of the vinyl ether. It is known that fluorocarbons having Cl or Br groups undergo metallation reactions to produce reactive intermediates. On the other hand, it is known that these substituents, particularly Cl, do not readily enter into reaction with nucleophiles. Thus the products would be unaffected in normal uses.

There is distinct benefit for having X'=Cl or Br. It is helpful to have Cl or Br in this position for the decarboxylation reaction. In decarboxylations of the prior art, compounds of the terminal functionality shown below are common.

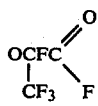

These materials generally require high temperatures and activators such as ZnO or silica to achieve reasonable yields to desired vinyl ethers.

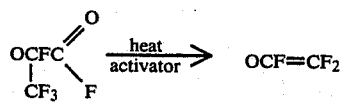

When X'=Cl or Br in the present invention, decarboxylation of these intermediates to vinyl ethers has been found to proceed under mild conditions and in excellent yields.

The variables have the following preferred values: n=1-6, a=0-3 and b=0-3. Even more preferred are compounds in which n=1-3. X is preferably Cl and X' is preferably Cl. $R_f$ and $R_f'$ are preferably F. Y is preferably $Z'SO_2$ and even more preferably Y=$Z'SO_2$ and Z'=F.

In general, the polymerization procedures and techniques followed in the present invention are known. A very good reference for polymerization techniques is *Emulsion Polymerization—Theory and Practice*, by D. C. Blackley, published by John Wiley & Sons.

Additionally, the copolymers used in the present invention may be prepared by general polymerization techniques developed for homo- and copolymerizations of fluorinated ethylenes, particularly those employed for tetrafluoroethylene which are described in the literature. Nonaqueous techniques for preparing the copolymers of the present invention include that of U.S. Pat. No. 3,041,317, to H. H. Gibbs, et al, that is by the polymerization of a mixture of the major monomer therein, such as tetrafluoroethylene, and a fluorinated ethylene containing sulfonyl fluoride in the presence of a free radical initiator, preferably a perfluorocarbon peroxide or azo compound, at a temperature in the range 0°-200° C. and at pressures in the range 1-200, or more atmospheres. The nonaqueous polymerization may, if desired, be carried out in the presence of a fluorinated solvent. Suitable fluorinated solvents are inert, liquid, perfluorinated hydrocarbons, such as perfluoromethylcyclohexane, perfluorodimethylcyclobutane, perfluorooctane, perfluorobenzene and the like.

Aqueous techniques which may also be used for preparing the copolymers used in this invention include contacting the monomers with an aqueous medium containing a free-radical initiator to obtain a slurry of polymer particles in non-waterwet or granular form, as disclosed in U.S. Pat. No. 2,393,967 to Brubaker or contacting the monomers with an aqueous medium containing both a free-radical initiator and a technologically inactive dispersing agent, to obtain an aqueous colloidal dispersion of polymer particles and coagulating the dispersion, as disclosed, for example, in U.S. Pat. No. 2,559,752 to Berry and U.S. Pat. No. 2,593,583 to Lontz.

Any one monomer represented by the general formula may be homopolymerized with itself or any one monomer may be copolymerized with any other monomer represented by the general formula. Additionally, more than two kinds of monomers represented by the general formula may be polymerized.

In addition, any one or more of the monomers represented by the general formula may be copolymerized with any one or more of the monomers selected from the group consisting of tetrafluoroethylene, trifluoromonochlorethylene, trifluoroethylene, vinylidene fluoride, 1,1-difluoro-2,2-dichloroethylene, 1,1-difluoro-2-chloroethylene, hexafluoropropylene, 1,1,1,3,3-pentafluoropropylene, octafluoroisobutylene ethylene, vinyl chloride, trifluoronitrosomethane, perfluoronitrosoethane and alkyl vinyl ether.

EXAMPLE 1

50 ml of dry tetraglyme and 8.0 grams anhydrous $Na_2CO_3$ were added to a 100 ml three-neck flask equipped with a stirrer, reflux condenser, thermometer, and a dropping funnel. Cold traps were located downstream of the reflux condenser. 35.67 grams of an acid fluoride product was analyzed and found to contain:

| Percent (wt.) | Compound |
|---|---|
| 12.8 | $FSO_2-(CF_2)_2-O-CF(CF_2Cl)-CF(F)=O$ |
| 57.4 | $FSO_2-(CF_2)_2-O-CF(CF_2Cl)-CF_2-O-CF(CF_2Cl)-CF(F)=O$ |
| 6.82 | $FSO_2-(CF_2)_2-O-[CF(CF_2Cl)-CF_2-O]_2-CF(CF_2Cl)-CF(F)=O$ |

It was added then dropwise over a three-hour period to the flask. The temperature rose slightly from room temperature to about 35° C. After $CO_2$ evolution ceased, a 30 inch vacuum was pulled on the system and the reactor was heated slowly until the pot reached 143° C. and the overhead temperature reached 99° C., 25.99 grams of product were collected. VPC analysis gave the following results:

| Percent (wt.) | Compound |
|---|---|
| 17.4 | $FSO_2-(CF_2)_2-O-CF=CF_2$ |
| 62.6 | $FSO_2-(CF_2)_2-O-CF(CF_2Cl)-CF_2-O-CF=CF_2$ |
| 2.4 | $FSO_2-(CF_2)_2-O-[CF(CF_2Cl)-CF_2-O]_2-CF=CF_2$ |

EXAMPLE 2

A 28 gram sample having the following mixture of acid fluorides

| Parts (wt.) | Compound |
|---|---|
| 1 | $FSO_2-(CF_2)_2-O-CF(CF_2Cl)-CF(F)=O$ |
| 26 | $FSO_2-(CF_2)_2-O-CF(CF_2Cl)-CF_2-O-CF(CF_2Cl)-CF(F)=O$ |
| 2.5 | $FSO_2-(CF_2)_2-O-[CF(CF_2Cl)-CF_2-O]_2-CF(CF_2Cl)-CF(F)=O$ |
| 2 | $FSO_2-(CF_2)_2-O-[CF(CF_2Cl)-CF_2-O]_3-CF(CF_2Cl)-CF(F)=O$ | was added dropwise to a slurry of 100 ml of freshly distilled tetraglyme and 5 grams $Na_2CO_3$ at 25° C. The mixture was stirred for one hour and then heat was applied slowly. At approximately 80° C., evolution of gas was observed. The products was collected by means of an ordinary Claisen still head with a side arm condenser and a receiver packed in dry ice on the side arm. A nitrogen purge was applied to exclude moisture initially. After gas evolution slowed at 95° C., the receiver was exchanged, a 28 inch Hg vacuum was applied and the temperature was raised to 135° C. for one hour. Collection was stopped and the two fractions analyzed.

Fraction one had 13.75 grams analyzing as

| Parts (wt.) | Compound |
|---|---|
| 1.7 | $FSO_2-(CF_2)_2-O-CF=CF_2$ |
| 21.7 | $FSO_2-(CF_2)_2-O-CF(CF_2Cl)-CF_2-O-CF=CF_2$ |
| 1 | $FSO_2-(CF_2)_2-O-[CF(CF_2Cl)-CF_2-O]_2-CF=CF_2$ |

Fraction two had 4 grams which was analyzed to be of the following composition:

| Parts (wt.) | Compounds |
|---|---|
| 3.8 | $FSO_2-(CF_2)_2-O-CF(CF_2Cl)-CF_2-O-CF=CF_2$ |
| 1 | $FSO_2-(CF_2)_2-O-[CF(CF_2Cl)-CF_2-O]_2-CF=CF_2$ |
| 1 | $FSO_2-(CF_2)_2-O-[CF(CF_2Cl)-CF_2-O]_3-CF=CF_2$ |

EXAMPLE 3

15 ml of tetraglyme and 1.0 gm of anhydrous $Na_2CO_3$ were added to a 3 neck flask equipped with a thermometer, stirrer and reflux condenser. Cold traps (−78° C.) were downstream of the condenser and a slight backpressure of $N_2$ was maintained by means of a bubbler. $FSO_2CF_2CF_2OCF(CF_3)CF_2OCF(CF_2Cl)CFO$ (3 gms) was added and after a brief evolution of $CO_2$, the temperature was raised to 80° C. and held there for several hours until $CO_2$ evolution ceased. A vacuum was pulled on the reactor and the temperature was slowly increased to 136° C. while collecting 1.5 gms of product in the cold trap. The majority of the product was collected before the temperature reached 90° C. VPC analysis showed addition product remaining in the tetraglyme solvent. The product, was confirmed as

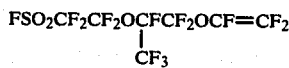

by Mass Spectrocopy, I.R. and F$^{19}$ NMR.

Using the procedures of the foregoing examples, the following functional fluorovinyl ethers are prepared:

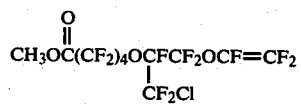

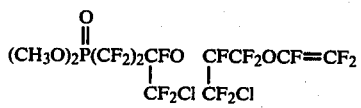

EXAMPLE 4

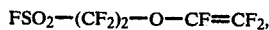

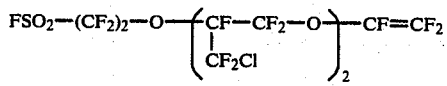

and tetrafluoroethylene were polymerized together as follows:

Ten grams of a mixture of FSO$_2$—(CF$_2$)$_2$—O—CF=CF$_2$ and

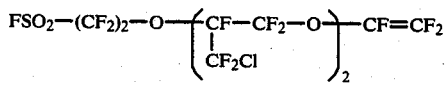

were added to 400 ml of a deoxygenated water solution containing 3 g K$_2$S$_2$O$_8$, 0.75 g NaHSO$_3$, 1.5 g Na$_2$HPO$_4$, and 3.5 g C$_7$F$_{15}$CO$_2$K soap in a glass-lined autoclave. The reaction was then carried out by maintaining a 60 psi tetrafluoroethylene pressure on the reactor for 16 hours with stirring at 10° C. The reactor was then vented, heated to 50° C. and evacuated to remove residual monomer. The contents were then frozen to coagulate the polymer which was filtered and rigorously washed after thawing. The dried polymer weighed 27.5 g. A film pressed from the polymer exhibited bands in the infrared absorption region associated with the —SO$_2$F group at 820 and 1465 cm$^{-1}$.

EXAMPLE 5

10 g of a mixture containing approximately two parts

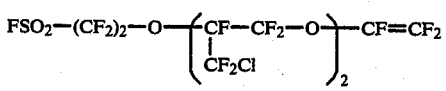

and one part

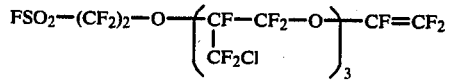

was added to a glass-lined, stirred stainless steel reactor containing 3 g K$_2$S$_2$O$_8$, 0.75 g NaHSO$_3$, 1.5 g Na$_2$HPO$_4$, and 3.5 g C$_7$F$_{15}$CO$_2$K. A 60 psi pressure of tetrafluoroethylene was then applied to the reactor and the temperature maintained at 20° C. for 1¾ hours. The reactor was vented, vacuum applied and heated to 50° C. to remove volatiles. The contents were then frozen, thawed and filtered followed by vigorous washing to remove inorganics and soap. The vacuum dried polymer weighed 7 g. Titration of a sample of the polymer, after hydrolysis from the —SO$_2$—F to the SO$_2$—ONa form using NaOH in a ethanol water mixture, gave a value of 3409 for the equivalent weight.

EXAMPLE 6

9.25 g of

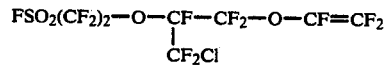

were added to 30 ml of ClCF$_2$—CCl$_2$F in a 100 ml stainless steel reactor. The contents were cooled to the freezing point and 2 drops of 2-tert.butylazo-2-cyano-4-methoxyl-4-methylpentane initiator solution added. The reactor was then evaporated and 8 g of tetrafluoroethylene added by condensation. The reactor was heated to 50° C. and shaken for 14 hours. The reactor was then vented and the solvent evaporate leaving a dried polymer residue of 4 g. The polymer was analyzed as containing 0.8% sulfur.

EXAMPLE 7

4.5 g of

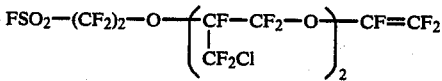

were added to 30 ml of ClCF$_2$—CFCl$_2$ in a 100 ml stainless steel reactor. The contents were cooled to the freezing point, 2 drops of 2-tert.butylazo-2-cyano-4-methoxyl-4-methylpentane initiator solution were added. The reactor was then evacuated and 8.25 g tetrafluoroethylene added by condensation. The reactor was then heated to 50° C. and shaken for 22 hours. The reactor was vented and the solvent evaporated, leaving a dried polymer residue of 7 g which analyzed as containing 0.6% sulfur.

We claim:

1. As a composition of matter, compounds represented by the formula

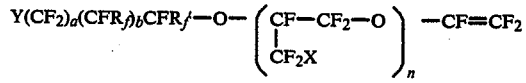

where
n=1 to 6;

X=Cl, Br or mixtures thereof when n>1

Y=an acid group or an acid derivative easily convertible to an acid group;

$R_f$ and $R_f'$ are independently selected from the group consisting of F, Cl, a perfluoroalkyl radical and a chlorofluoroalkyl radical;

a=0 or an integer greater than 0;

b=0 or an integer greater than 0.

2. The compounds of claim 1 where Y is selected from the group consisting of Z'SO$_2$,

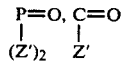

and C≡N where
Z' is F, Cl, Br, OH, NRR' or OA,
R and R' are independently selected from the group consisting of hydrogen, an alkyl having one or more carbon atoms and an aryl;
A is an alkali metal, quaternary nitrogen radical, or R.

3. The compounds of claim 2 where Y is Z'SO$_2$.
4. the compounds of claim 3 where Z' is F.
5. The compounds of claim 2 where a=0-3; b=0-3; n=1 to 6; $R_f$=F or Cl and $R_f'$=F or Cl.
6. The compounds of claim 2 where Y=COZ'.
7. The compounds of claim 2 where n=1.
8. The compounds of claim 2 where n=1 and X=Cl.
9. The compounds of claim 3 where X=Cl.

* * * * *